(12) United States Patent
Cohen et al.

(10) Patent No.: US 8,980,609 B2
(45) Date of Patent: Mar. 17, 2015

(54) UNIFORMLY CONJUGATED SERINE HYDROLASES

(75) Inventors: Ofer Cohen, Moshav Netaim (IL); Chanoch Kronman, Rehovot (IL); Baruch Velan, Tel-Aviv (IL); Avigdor Shafferman, Nes-ziona (IL)

(73) Assignee: Israel Institute for Biological Research, nes Ziona (IL)

( * ) Notice: Subject to any disclaimer, the term of this patent is extended or adjusted under 35 U.S.C. 154(b) by 725 days.

(21) Appl. No.: 11/916,483

(22) PCT Filed: Jun. 8, 2006

(86) PCT No.: PCT/IL2006/000669
§ 371 (c)(1),
(2), (4) Date: May 14, 2008

(87) PCT Pub. No.: WO2006/137052
PCT Pub. Date: Dec. 28, 2006

(65) Prior Publication Data
US 2009/0068165 A1    Mar. 12, 2009

(30) Foreign Application Priority Data
Jun. 23, 2005 (IL) .......................... 169377

(51) Int. Cl.
*C12N 9/14* (2006.01)
*C12N 9/18* (2006.01)
*A61K 47/48* (2006.01)

(52) U.S. Cl.
CPC ............ *C12N 9/18* (2013.01); *A61K 47/48215* (2013.01); *C12Y 301/01007* (2013.01)
USPC .......................................... 435/195; 435/188

(58) Field of Classification Search
CPC ...................... C12Y 301/01; C12Y 301/01008
USPC ........................................................ 435/195
See application file for complete search history.

(56) References Cited

U.S. PATENT DOCUMENTS

| | | | |
|---|---|---|---|
| 6,753,149 B2 | 6/2004 | Bailey et al. | |
| 2004/0082765 A1 | 4/2004 | Nakamura et al. | |
| 2005/0114037 A1 | 5/2005 | Desjarlais et al. | |
| 2009/0249503 A1* | 10/2009 | Rosendahl ...................... | 800/13 |

FOREIGN PATENT DOCUMENTS

| WO | WO 02/087624 | 7/2002 |
|---|---|---|
| WO | 2006/063055 | 6/2006 |

OTHER PUBLICATIONS

Andreopoulos et al. (Biotechnology and Bioengineering, vol. 65, No. 5, pp. 579-588, 1999).*
Kronman C. et al.: Biochem. J. 311 (1995) 959-67.
Chitlaru T. et al.: Biochem. J. 336 (1998) 647-58.
Cohen O. et al.: Biochem. J. 378 (2004) 117-28.
Onda M. et al.: Bioconjugate Chem. 14 (2003) 480-7.
Kryger G. et al: Act. Cryst D56 (2000) 1385-94.
Velan B. et al.: J. Biol. Chem. 266 (1991) 23977-84.
Kronman C.et al.: Gene 121 (1992) 295-304.
Ellman G..L. et al.: Biochem. Pharmacol. 7 (1961) 88-95.
Cohen O. et al.: Biochem. J. 357 (2000) 795-802.
Tsusumi Y. et al.: Proc. Natl. Acad. Sci. USA 97 (2000) 8548-53.
Shafferman A. et al. J. Biol. Chem. (1992) 17640-48.
Ordentlich A. et al.: J. Biol. Chem. 271 (1996) 11953-62.
Shafferman A. et al.: Biochem. J. 318 (1996) 833-40.
Kovarik, Z. et al: "Mutant chlinesterases possessing . . . conjugates" Biochemistry Mar. 23, 2004, pp. 3222-3229.
Barak, D. et al: "Evidence for P-N bond . . . acetylcholinesterase" Biochemistry Feb. 8, 2000, pp. 1156-1161.
EPO supplementary search report—11 pages—mailed on Jul. 23, 2010.
Kryger et al.; Structures of recombinant native and E202Q mutant human acetyl-cholinesterace complexed with the snake-venom toxin faciculin-II, Biological Crystallography, (2000) 1385-1394.
U.S. Army Medical Research and Materiel Command; Contract No. DAMD17-03-C-0012; Annual report: A820534 (Apr. 2005);Generation of Recombinant Human AChE OP-Scavengers with Extended Circulatory Longevity; A. Shafferman.
U.S. Army Medical Research and Materiel Command; Contract No. DAMD17-03-C-0012; Annual report: A117324 (Apr. 2004);Generation of Recombinant Human AChE OP-Scavengers with Extended Circulatory Longevity; A. Shafferman.
Vanwetswinkel, S et al. "Blood" (2000) 95, pp. 936-942.
Kinstler, O et al. "Adv Drug Deliv Rev" (2002) 54; pp. 477-485.

* cited by examiner

*Primary Examiner* — Tekchand Saidha
(74) *Attorney, Agent, or Firm* — Roach Brown McCarthy & Gruber, P.C.; Kevin D. McCarthy

(57) ABSTRACT

An organophosphate scavenger is provided, with extended residence time in the mammalian circulation, which can be used in preventive and therapeutic treatment of organophosphate poisoning. The scavenger is a uniformly pegylated serine hydrolase, in which a part of lysine residues were replaced with other residues by site-directed mutagenesis. One part of lysine residues in the hydrolase amino acid sequence is selected for the PEG-coupling, and the other part for the replacement, wherein the selection should ensure that the hydrolase surface shows at least one free amino acid for PEG coupling for all possible views obtained by rotating a 3-D model generated for the hydrolase.

23 Claims, 9 Drawing Sheets

Table 1

| AChE type | Spec. act. (U/μg) | T₁/₂ at 51°C (min.) |
|---|---|---|
| WTΔC-AChE (548aa) | 6.5 | 8.9 |
| K23A | 12.0 | 10.2 |
| K53A | 4.1 | 8.4 |
| K332A | 4.5 | 3.1 |
| K348A | 2.2 | 4.6 |
| K470A | 6.3 | 1.5 |
| K496A | 20.0 | 8.9 |
| K538A | 5.7 | 4.6 |
| K23A/K332A | 10.8 | 3.3 |
| K23A/K348A | 4.0 | 4.9 |
| K332A/K348A | 2.5 | 3.0 |
| K470A/K496A | 12.7 | 1.3 |
| K23A/K332A/K348A | 2.5 | 2.6 |
| K23A/K332A/K470A | 5.0 | 0.6 |
| K23A/K348A/K470A/K496A | 2.5 | 0.6 |
| K23A/K332A/K496A/K538A | 2.6 | 3.0 |
| K23A/K53A/K332A/K348A/K496A | 1.3 | 2.9 |
| K23A/K332A/K348A/K470A/K496A | 2.7 | 0.6 |
| K23A/K53A/K332A/K348A/K496A/K538A | 1.6 | 1.5 |
| K23A/K53A/K332A/K348A/K470A/K496A/K538A | 5.7 | 0.5 |

Fig. 2

Table 2

| PEG target sites | #PEG per AChE subunit | MRT Mice (minutes) | MRT Monkeys (minutes) | Mutant type |
|---|---|---|---|---|
| all lysines/N-terminus | 4-5 | 2100±170 | 9730±820 | Wild type |
| K53/K470/K496/K538/N-terminus | 5 | 1795±420 | 9360±650 | K23A/K332A/K348A |
| K53/K348/K496/K538/N-terminus | 5 | 1730±320 | 9140±390 | K23A/K332A/K470A |
| K53/K332/K538/N-terminus | 4 | 1860±140 | 8750±270 | K23A/K348A/K470A/K496A |
| K53/K348/K470/N-terminus | 4 | 1740±210 | 8480±250 | K23A/K332A/K496A/K538A |
| K470/K538/N-terminus | 3 | 1320±120 | 4120±130 | K23A/K53A/K332A/K348A/K496A |
| K53/K538/N-terminus | 3 | 770±70 | 3210±120 | K23A/K332A/K348A/K470A/K496A |
| K470/N-terminus | 2 | 520±30 | 1690±90 | K23A/K53A/K332A/K348A/K496A/K538A |
| N-terminus | 1 | 365±20 | 340±25 | K23A/K53A/K332A/K348A/K470A/K496A/K538A |
| None | 0 | 42±4 | 210±75 | Non-pegylated wild type |

Fig. 5

Generation of α-AChE antibodies in monkeys

PEGylation of AChE lysine mutants

AChE mutant: Non-PEGylated | K470 | K53/K538 | K470/K538 | K53/K348/K470 | K53/K332/K538 | K53/K348/K496/K538 | K53/K470/K496/K538 kDa markers: 200, 150, 100, 75

No. of PEGs: 0, 2, 3, 3, 4, 4, 5, 5

Fig. 10

UNIFORMLY CONJUGATED SERINE HYDROLASES

CLAIM OF PRIORITY

This application claims priority as a 371 of international application serial number PCT/IL2006/000669 filed on Jun. 8, 2006; which claims priority to Israeli patent application serial number 169377 filed on Jun. 23, 2005.

FIELD OF THE INVENTION

The present invention relates to homogeneously conjugated serine hydrolases with maximal pharmacokinetic performance and maximal immunological tolerance, particularly to pegylated cholinesterases, utilizing hypolysine-mutant arrays.

BACKGROUND OF THE INVENTION

The primary role of acetylcholinesterase (AChE) is the termination of impulse transmission in cholinergic synapses by rapid hydrolysis of the neurotransmitter acetylcholine (ACh). Some organophosphate (OP) compounds, such as the nerve agent sarin and soman, or agricultural pesticides, inhibit cholinesterases (ChEs), such as acetylcholinesterases (AChEs) and butyrylcholinesterases (BChEs), by rapid phosphylation of the serine residue in the enzyme active site. The acute toxicity of these OP agents leads to motor and respiratory failure due to the inhibition of AChE in the peripheral and central nervous system.

The high reactivity of ChEs towards OP-agents led to propose these biomolecules, as exogenous scavengers for sequestration of toxic OP-agents, or as destroyers, before they reach their physiological target. However, a large-scale production of suitable serine hydrolases with OP scavenging and hydrolytic activity is obstructed by the fact that recombinant enzymes of various origins are relatively short-lived in the circulation of experimental animals [e.g., Kronman C. et al.: Biochem. J. 311 (1995) 959-67; Chitlaru T. et al.: Biochem. J. 336 (1998) 647-58]. In a controlled conjugation of polyethylene glycol (PEG) moieties to the C-terminal truncated version of recombinant human AChE ($\Delta$C-rHuAChE), we increased the life-time of the enzyme activity in the circulation of mice (WO 02/087624). Examination of pharmacokinetic performance of an array of PEGylated (=pegylated) AChEs which differed one from another by their degree of modification, as well as by the length of the appended PEG chains, demonstrated that circulatory residence of the enzyme was significantly improved, and that the mean residual time (MRT) was increased as high as 50-fold when compared to the MRT of nonmodified rHuAChE. MRT, reflecting the average length of time of retaining the administered molecules by the organism, is obtained by analyzing the clearance data according to a non-compartmental pharmacokinetic model, as opposed to the half-life value, which is derived by fitting the clearance profile to a bi-exponential pharmacokinetic model. Said modified HuAChE exhibited MRT values of 2100 minutes and more in mice. Such values are unmatched by any other known form of recombinant or native plasma derived cholinesterase (ChE) reported to date in mice. The maximal MRT values reported in mice for serum derived human BChE, horse BChE, or fetal bovine AChE, have been approximately 1,400 minutes [e.g., Kronman C. et al.: Biochem. J. 311 1995) 959-67]. We have further demonstrated the increase of circulatory residence of pegylated rHuAChE in rhesus macaques [Cohen O. et al.: Biochem. J. 378 (2004) 117-28)].

The substantial increase in the pharmacological stability of ChEs, mentioned above, has removed an obstacle on the way toward utilizing serine hydrolases as organophosphates scavengers. However, an enzyme-based detoxifying agent for pharmaceutical uses should exhibit, beside improved stability and retained activity, preferably also a well defined composition. A desired agent for a pharmaceutical use should preferably comprise one chemical structure, but pegylation of a protein provides a heterogeneous product corresponding to a mixture of various structures comprising randomly formed linkages of PEG with reactive sites, such as lysine 1-amino groups, that are available on the protein molecule. If, for example, a protein has 8 free amino acids, similarly accessible for coupling with PEG molecules, theoretically 256 different combinations may be obtained. Although in practical cases not all possibilities will be realized with the same probability, a heterogeneous composition will be obtained, macroscopically appearing usually as more components. It is therefore an object of this invention to provide a uniformly pegylated preparation of serine hydrolase.

US Patent Application 2004/0082765 describes erythropoietin conjugated with one PEG chain at one position only, taking advantage of low number of available amino groups in the protein. However, in general cases there are many free attachment sites available, and furthermore, it is usually preferable to couple more than one polymer chain to the protein. It is therefore another object of this invention to provide a general method for the preparation of uniformly pegylated serine hydrolases comprising any predetermined number and any predetermined locations of the attachment sites.

Onda et al. [Onda M. et al.: Bioconjugate Chem. 14 (2003) 480-7] described the preparation of mutants of a recombinant immunotoxin with diminished number of lysine residues for eventual pegylation, and assessed the effect of the mutations on the residual immunotoxin activity. US Patent Application 2005/0114037 relates to a computational method predicting how the location and type of coupling might decrease specific activity of said protein. This invention is directed predominantly to decreasing immunogenicity of a conjugated protein. It is also an object of the invention to provide a method for the preparation of uniformly pegylated serine hydrolase with organophosphate scavenging or hydrolytic activity with lowered immunogenicity, comprising steps of predetermining the number and the location of the conjugated PEG chains, possibly utilizing three-dimensional structures of mutants lacking certain free amino groups present in the wild type, and selecting suitable mutants according to accessibility of the free amino groups for eventual coupling.

It is still another object of this invention to provide a homogeneous preparation of pegylated serine hydrolase exhibiting extended circulatory residence time in the mammalian circulation.

It is a further object of this invention to provide a uniformly pegylated preparation of acetylcholinesterase displaying mean residence time (MRT) values of 1000 minutes or more in the mouse circulation or 4000 minutes or more in the circulation of primates.

It is a still further object of this invention to provide a method for producing uniformly pegylated AChE, exhibiting sufficient activity and circulatory longevity in the circulation of primates.

It is also another object of this invention to provide a homogeneous agent based on pegylated AChE for use in scavenging organophosphates (OPs).

This invention also aims at providing the use of pegylated AChE in preventive and therapeutic treatment of OPs poisoning.

It is also an object of this invention to provide a pharmaceutical composition for treating or preventing OPs poisoning, which composition exhibits low immunogenicity.

Other objects and advantages of present invention will appear as description proceeds.

SUMMARY OF THE INVENTION

The present invention provides a uniformly PEG-conjugated (pegylated) hypolysine mutant serine hydrolase with organophosphate scavenging and/or hydrolytic activity, in which the PEG chains are preferably conjugated at predetermined sites of the molecule of said enzyme. The PEG chains are conjugated to ε-amino groups of all remaining lysine residues of said hypolysine mutant. Said hypolysine mutant may be obtained by known techniques of site-directed mutagenesis. All lysine residues in the protein molecule, except for predetermined number of lysine residues, preferably three or four lysine residues, are replaced by another amino acid residue. This another residue may be any amino acid residue that does not have deleterious effect on the enzyme desired properties, or does not interfere with the conjugating process. In a preferred embodiment of the invention, said hydrolase is cholinesterase, which may be selected from acetylcholinesterases and butyrylcholinesterases. Pegylated serine hydrolases of the invention has a sufficient hydrolytic activity, and preferably its specific activity is at least about 10% of hydrolase specific activity of the non-mutated non-pegylated enzyme. The pegylated enzyme of the invention has reduced immunogenicity, and it has increased longevity in the mammalian circulation.

The present invention provides a method for the preparation of a uniformly pegylated hypolysine mutant serine hydrolase, comprising providing a serine hydrolase with organophosphate scavenging or hydrolytic activity with known amino acid sequence; selecting the number of PEG chains to be conjugated to the molecule of said hydrolase, and selecting the location of the conjugated chains within said sequence; effecting site-directed mutagenesis of said hydrolase, and replacing all lysine residues in the molecule by other amino acid residues, except those lysine residues predetermined in step ii) for conjugating the PEG chains, thereby to obtain a hypolysine mutant of said hydrolase; reacting the hypolysine mutant from step iii) with activated PEG; thereby to obtain a uniformly conjugated serine hydrolase with organophosphate scavenging or hydrolytic activity with lowered immunogenicity, and increased stability and longevity in the mammalian circulation. In one embodiment, the invention provides a method for the preparation of a protein, having desired hydrolase activity, conjugated uniformly via free amino groups with a polymer, comprising i) providing a protein with a known amino acid sequence; ii) selecting all possible mutants in which all but n−1 lysine residues are replaced by another amino acid residue, and which have n free amino groups left, including the terminal amino group, for a conjugating reaction, wherein the initial value of n is 3 (dilysine-enzyme); iii) generating a three dimensional structure for each of said mutants of step ii), optionally with corresponding two-dimensional representation, comprising marked positions for the terminal amino group and the amino groups of lysine residues; iv) examining each mutant of step iii) by rotating its structure sequentially around the X-axis by 90°, Y-axes by 90°, and Z-axes by 90°, providing 12 different rotational positions and 12 corresponding two-dimensional front views, evaluating each position as positive if there is at least one free amino group inside the front view, and as negative if there is no free amino group inside the front view; v) discarding all the mutants evaluated as negative in at least one of said 12 rotational positions, and selecting one of the mutants evaluated as positive in all 12 positions for real mutant construction; or, if all the potential mutants were discarded, continuing by step ii) in which the value of n is increased by 1 (trilysine-enzyme and higher) through steps iii to v; vi) constructing said selected mutant from step v) by using known methods for mutating and expressing recombinant proteins, thereby obtaining a recombinant hypolysine enzyme mutant; and vii) reacting said mutant from step vi) with a non-immunogenic polymer under conditions enabling to couple a chain of said polymer to each of said free amino groups; thereby to obtain uniformly conjugated protein with lowered immunogenicity, and increased stability in mammalian circulation. A method according to the invention preferably further comprises viii) repeating said steps ii to vii, while using more values of n in order to obtain more uniformly conjugated mutant proteins; and ix) evaluating the conjugated mutant proteins to determine a desired property; and x) selecting the best one for a large scale production. Said desired properties comprise one or more items selected from specific activity, thermal stability, antigenicity, immunogenicity, and stability in mammalian circulation. Said amino acid which replaces lysine in step ii) may be alanine, or any other amino acid representing a neutral replacement, i.e. a replacement which will not have a negative effect on the desired properties of the conjugate. Beside mutating the protein at site of lysine residues, to prevent coupling in those positions, in some embodiments of the invention also other mutations are effected to further improve the product or adjust the properties of the resulting conjugate to its intended function; or alternatively other mutations, or modifications, may be effected to prevent coupling PEG through other groups of the protein than lysine residues.

In a preferred embodiment of the invention, said pegylated hydrolase is an AChE conjugate comprising PEG. Of course, other polymers, such as dextran, polyvinyl pyrrolidone, polyacrylamide, polyvinyl alcohol, and other polyalkylene oxides might be used in a similar mode as described for the method of the invention. In a preferred embodiment of the invention, said polymer comprises a polyethylene glycol (PEG), such as activated methoxy-PEG. Said PEG may have a molecular weight of from about 200 to about 100,000 dalton, such as from about 2000 to about 40,000 dalton, preferably from about 5000 to about 20,000 dalton. In a preferred embodiment, the method of the invention provides uniformly pegylated AChE, wherein said values n in step ii) of the method are from 3 to 5. Said AChE is preferably human AChE in which from 3 to 5 lysine residues are replaced by alanine residues, and in which phenylalanine at position 338 may be further replaced by alanine. The pegylated AChE provided by the method may have a mean residence time value in the mouse circulation of 1000 minutes or more.

The invention is further directed to uniformly pegylated AChE. A uniformly pegylated AChE according to the invention may comprise from 3 to 6 PEG chains coupled at predetermined sites via remaining amino groups to AChE mutant in which from 2 to 5 lysine residues are replaced by other amino acid. The pegylated AChE of the invention has reduced immunogenicity, and increased stability in mammalian circulation. Preferred pegylated AChE of the invention is pegylated human AChE recombinant enzyme. In one preferred embodiment, pegylated AChE enzymes comprise the replacements of lysine by alanine at positions K23, K332, and K348; or K23, K332, and K470; or K23, K348, K470, and K496; or K332, K496, and K538. In one preferred embodiment of the invention, a uniformly pegylated AChE further comprises replacement of phenylalanine by alanine at position 338.

In another aspect, the invention provides a uniformly pegylated AChE as described above for use as an organophosphate (OP) scavenger, or as a detoxifying agent.

The invention is also directed to the use of uniformly pegylated hypolysine mutant serine hydrolase (e.g. AChE, BChE, paraoxonase, phosphotriesterase) with organophosphate scavenging or hydrolytic activity in the preparation of a pharmaceutical composition for treating or preventing OP poisoning. In a preferred embodiment, said hydrolases is AChE.

The invention provides a pharmaceutical composition for treating or preventing OP poisoning, comprising uniformly pegylated hypolysine mutant serine hydrolase with organophosphate scavenging or hydrolytic activity, optionally further comprising pharmaceutically acceptable carrier, diluent, adjuvant, or excipient. In a preferred embodiment of the invention, said hydrolase is AChE or BChE.

In still another aspect, this invention provides a method for increasing the circulatory half-life of an active AChE of a known amino acid sequence comprising i) generating three dimensional structures for potential mutants of said AChE in which only from 2 to 4 lysine residues are left, and the other lysine residues are replaced by alanine, ii) rotating each of the structures sequentially around the X-axis by 90°, around Y-axes by 90°, and around Z-axes by 90°, providing 12 different rotational positions and 12 corresponding two-dimensional front views for each structure; and accepting only the potential mutants that show at least one free amino group inside the front view in all examined 12 rotational positions; and discarding the remaining tentative mutants; iii) constructing one or more real mutants with predetermined number and location of lysine-alanine replacements as accepted in step ii; and iv) reacting the mutant(s) from step iii) with an activated non-immunogenic polymer under conditions enabling to couple said polymer to all free amino groups in AChE; thereby to obtain uniformly pegylated AChE with lowered immunogenicity, and with increased stability in mammalian circulation.

BRIEF DESCRIPTION OF THE DRAWINGS

The above and other characteristics and advantages of the invention will be more readily apparent through the following examples, and with reference to the appended drawings, wherein:

FIG. 2. is a table showing thermal stabilities and specific activities of C-terminal truncated recombinant human AChE (ΔC-AChE) mutants replacing lysine by alanine in various positions, and of the wild type;

FIG. 5. is a table showing mean residual time (MRT) values in mice and in monkeys for several pegylated species of ΔC-AChE mutants replacing lysine by alanine in various positions, and of the wild type;

FIG. 10. is the analysis of a uniformly conjugated enzyme according to the invention by SDS-PAGE.

DETAILED DESCRIPTION OF THE INVENTION

Figure 1:
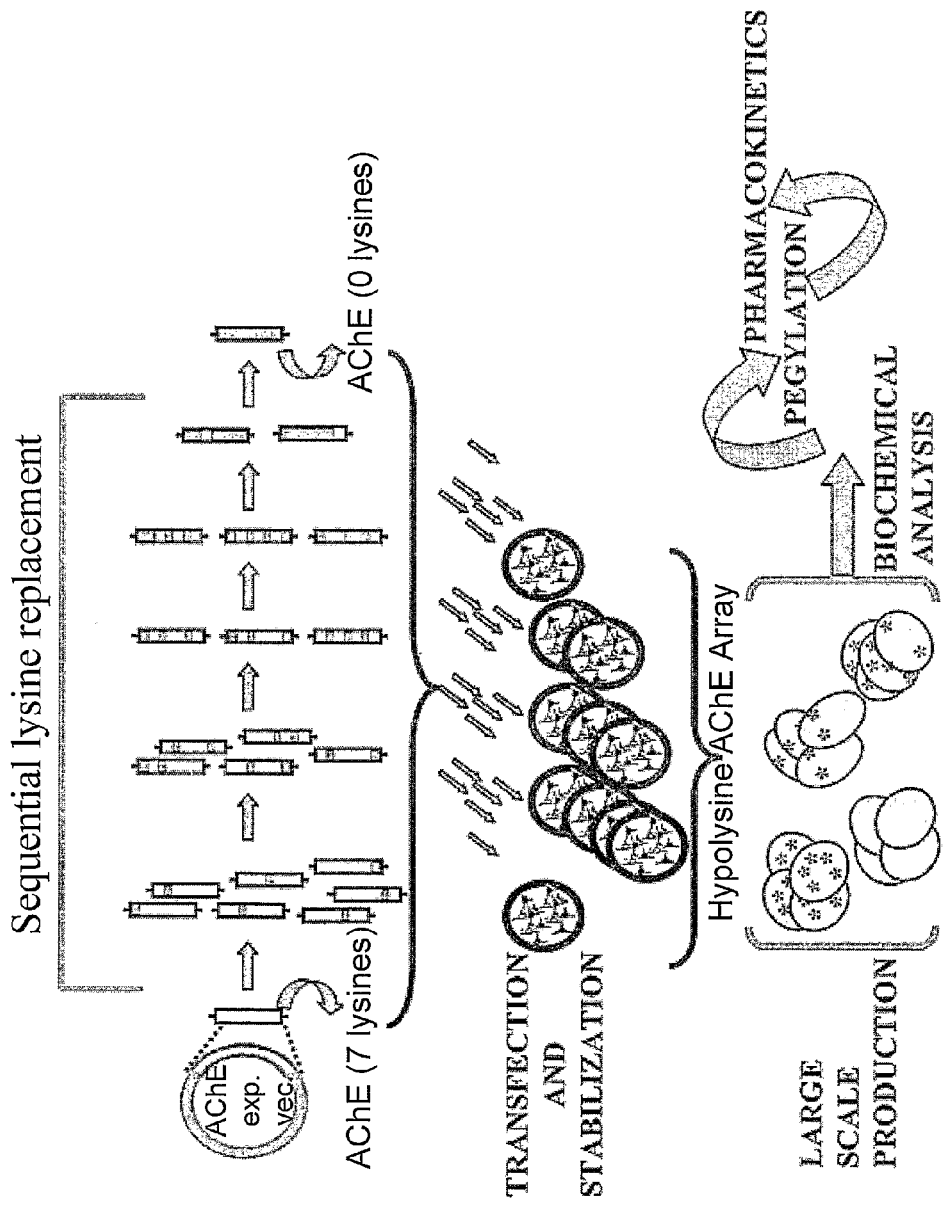
FIG. 1. is a scheme illustrating the selection of various AChE species and their production.

A method is now being provided that enables to rationally design a pegylated acetylcholinesterase (PEG-AChE) for use in pharmaceutical compositions. A PEG-AChE according to the invention is a sufficiently active homogeneous material with a long residence time in the mammalian circulation. Said homogeneity and said circulation stability are achieved by selecting a suitable combination of free amino groups in the AChE protein for coupling with a non-immunogenic polymer chain, removing non-selected free amino groups, except for the terminal amino group, from said AChE protein by targeted mutation of the amino acid sequence of the protein, and coupling all remaining free amino groups in the mutated AChE with said polymer chain. Said selecting a suitable combination may comprise, advantageously, constructing the three-dimensional (3D) model of said AChE and locating said free amino groups on the surface of said 3D model.

Said rational design is enabled by combining several our observations, some of which might seem quite surprising. First of all, we prepared several mutants of the working enzyme (ΔC-AChE) with lysine residues replaced by alanine, in search for lysine residues which might be essential for the activity or stability of the enzyme, and it was found that no lysine residue was essential (see, e.g., FIG. 2). In order to differentiate between many possible mutants from viewpoint of their potential pharmaceutical application, and while intending to reduce the immunogenicity of the mutants and to increase their half-life in the plasma by attaching a non-immunogenic polymer to the protein surface using a known amino-coupling chemistry, we constructed theoretical 3D structures using SYBYL modeling software, and we located and marked the free lysine amino groups within said theoretical structures. Supposing that covering the surface of said protein by said polymer would reduce accessibility of the enzyme for the factors that might neutralize its activity, such as e.g. antibodies, and wondering which criterion might be applied in selecting the right combination of the attachment points for the shielding polymer on the model surface, we rotated the 3D model of ΔC-AChE with marked free amino groups. Finally, we formulated the following condition: when repeatedly rotating the model by 90°, no face turned to the viewer should be devoid of free amino groups (potential attachment points). A comparison of several mutants we constructed corroborated practical value of said tentative criterion; mutants whose model structure provided at least one empty face during rotating by 90° turned out to be less pharmacokinetically stable than the mutants whose model structure provided only non-empty faces. Based on the above model, several C-terminal truncated recombinant human AChE (ΔC-AChE) mutants have been constructed and pegylated. The pharmacokinetic measurements have shown remarkable stability in both mouse and monkey circulation. Furthermore, the obtained products have been found to be homogeneous materials, suitable for pharmaceutical applications.

Figure 4:
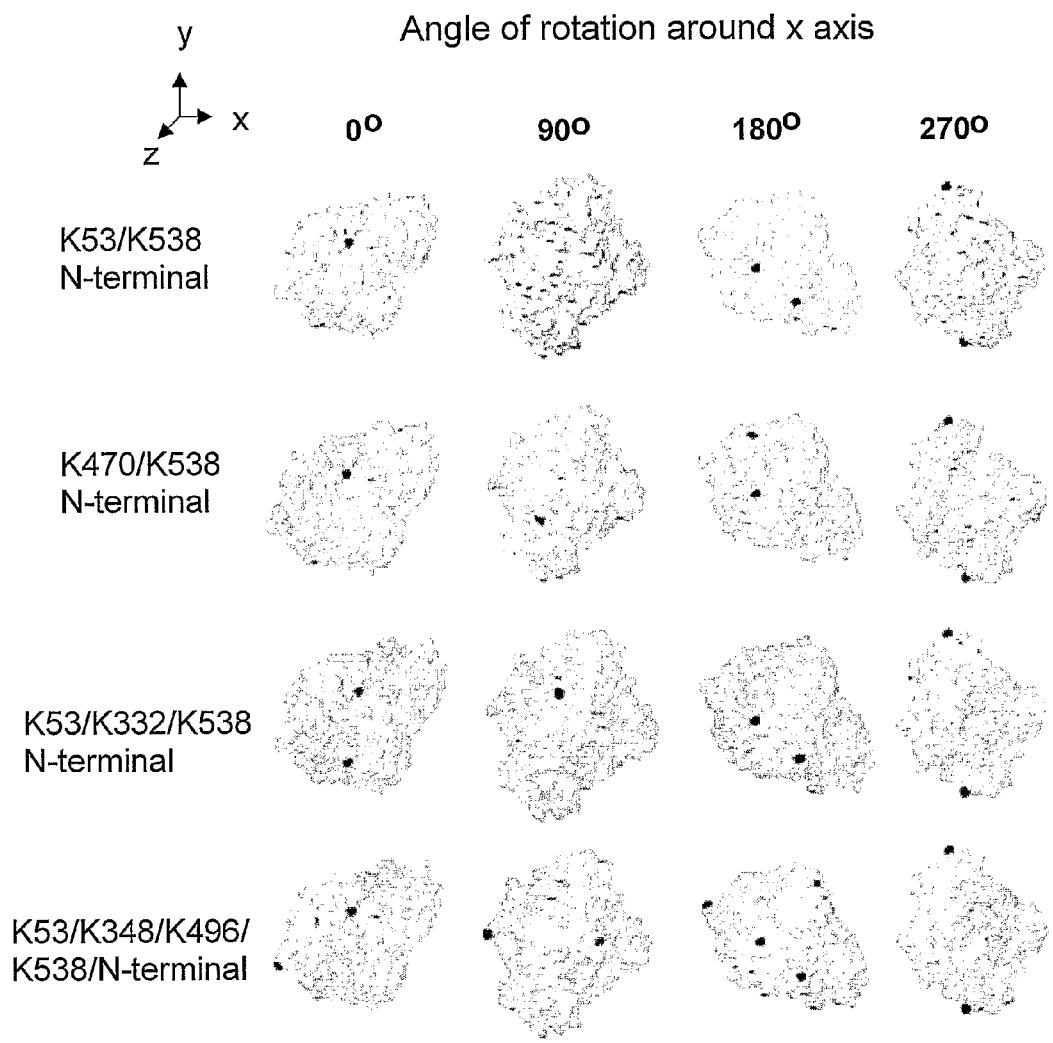
FIG. 4. shows 3D models of ΔC-AChE constructed by means of SYBYL modeling software, with marked positions for specified lysine residues.

Thus the determination of the spatial locations of the lysine residues within the 3D model of AChE served as a guideline for selecting the combination of mutation sites, and for the sites of PEG attachment. The working hypothesis, taking into consideration the importance of an efficient coverage of the macromolecular surface by PEG chains, and employing simulated rotation of macromolecule models around principal axes, has proved useful; there should always be at least one anchoring point (PEG target site) present at the surface. For example, the rotation of two different dilysine-AChE configurations, comprising doublet of remaining lysines at positions 53 and 538 (with five remaining lysine residues replaced by alanine) and at positions 470 and 538 (FIG. 4), around the X-axis demonstrated that while the K53/K538 enzyme presented a hemispherical surface devoid of any anchoring point, no such empty surface could be observed for the K470/K538 enzyme (rotations around other axes yielded equivalent results for both enzyme forms, with no empty surfaces). The latter mutant might be expected to be covered after pegylation on all faces by the shielding polymer, whereas the former mutant would be exposed to deleterious effects at least on one of its faces. And indeed the latter mutant has been shown to last in the mouse circulation nearly twice as long as the former mutant (FIG. 5).

We further surmised that the inclusion of more than one anchoring point per surface will contribute to enzyme surface coverage to a lesser degree, and therefore, e.g., in the case of the K53/K332/K538 enzyme, where the surface at 0° rotation displays 2 lysine residues instead of 1 lysine as in the K470/K538 enzyme (FIG. 4), pharmacokinetic performance will be only moderately greater. Further addition of anchoring points was not expected to significantly enhance enzyme coverage, suggesting that the K53/K348/K496/K538 enzyme, comprising five PEG chains (four lysines and one terminal amino group), would not display pharmacokinetic performance much better than K53/K332/K538, having four PEG chains. The above predictions based on this sort of analysis were corroborated in pharmacokinetic experiments carried out in rodents and in non-human primates (see FIG. 5). Thus, the guidelines provided by the invention, resulting from considering the surface coverage, will be useful for masking epitopes, or post-translation modification determinants, or other sites of potential interaction on proteins, glycoproteins, lipoproteins, etc.

A skilled person is aware that the principles proved on the example of AChE hold also for other proteins. Therefore, in one aspect the invention is directed to a method for lowering immunogenicity of a protein, such as serine hydrolases, by conjugating it uniformly via free amino groups to a polymer, such as PEG, wherein the conjugation occurs at predetermined attachment sites. The method of the invention is applicable for a protein of a known sequence, and comprises selecting the sites of the conjugation in the protein, comprising preferably evaluating all hypothetical mutants in which lysine residues are replaced by another amino acid residue at all positions but at selected sites, leaving n−1 free amino groups left, providing together with the terminal amino group n sites for the conjugating reaction. Such mutants that have less than 4 free amino groups are less preferred, meaning that the initial value of n is preferably 4. Such mutant contains three lysine residues (trilysine-protein), and after pegylation may contain 4 PEG chains per protein molecule. The method of the invention may utilize the generation of a three dimensional structure for each of considered mutants, using known computation methods, and preferably presents the computed structures in a two-dimensional representation, with the positions of free amino groups clearly marked on the representation. Each considered 3D structure is rotated sequentially around three principal axes, by 90°, using available programs, and each of 12 possible representations are evaluated for the presence of a free amino group on the protein face (an attachment point, accessible for coupling). The evaluation of the positions may be performed manually or may be automatized. Each face containing at least one free amino group is denoted as positive, all other faces as negative. A protein structure whose all rotational representations are positive is accepted as a good candidate for constructing a real mutant protein and for pegylation, all other structures are rejected and discarded. When there are only few free amino groups, or if the free amino groups are concentrated close to each other, it may happen that all considered mutants have been discarded; in that case 5 or more lysine residues are retained in the considered mutants, producing tetralysine-protein, pentalysine-protein, etc. After this simulation work, selected combinations are materialized by using known methods for mutating and expressing recombinant proteins, thereby obtaining one or more recombinant hypolysine enzyme mutants to be optionally characterized, and then reacted with an activated non-immunogenic polymer, such as PEG.

This approach for determining optimal target sites for PEG-conjugation might be employed for other proteins of therapeutic interest (e.g. BChE, paraoxonase, phosphotriesterase), whenever the conversion is required into a long-lived circulatory molecule, or when the immunological tolerance should be increased, or when the interactions of the modified protein with any given receptor should be reduced. A skilled person is also aware of the fact, and will take it into consideration, that the conjugation of activated polymers to a protein occurs not only at the sites of lysine residues, but possibly also at other reactive groups, such as terminal amino group or non-oxidized cysteine residue, etc.

The invention enables employing conjugated proteins (e.g. AChE, BChE, paraoxonase, phosphotriesterase) in pharmaceutical compositions as well defined, homogeneous materials. FIG. 10 illustrates the preparation of homogeneous products according to the invention. Particularly, pegylated acetylcholinesterases are now available as active, non-immunogenic, homogeneous materials for scavenging, detoxifying, or other biological functions.

The invention will be further described and illustrated in the following examples.

EXAMPLES

Construction, Generation and Production of a Series of Hypolysine AChE Mutants

The C-terminal truncated version of recombinant human AChE was prepared as described, [Kryger G. et al: Act. Cryst D56 (2000) 1385-94]. The DNA coding sequences for the truncated HuAChE (ΔC-HuAChE) was inserted into a tripartite expression vector expressing also the reporter gene cat and the selection marker neo [Velan B. et al.: J. Biol. Chem. 266 (1991) 23977-84; Kronman C. et al.: Gene 121 (1992) 295-304]. A series of different hypolysine AChE expression vectors were constructed. Seven constructs in which a single lysine residue was replaced by alanine (K23A, K53A, K332A, K348A, K470A, K496A, K538A) were generated by site-directed mutagenesis. Twelve constructs in which 2-7 lysine residues were replaced by alanine (FIG. 1) were generated by exchange of the relevant fragments between the single lysine mutants.

The generation of stably transfected HEK-293 cell lines expressing high levels of rHuAChE and rHuAChE mutants and purification of the secreted enzymes were performed as described previously [Velan B, ibid; Kronman C, ibid].

Determination of Thermostability and Specific Activity of Hypolysine AChE Mutants The elimination of key lysines, such as those that participate in essential salt-bridges, may result in a severe impairment of the architecture and biological function of proteins. The rationalized elimination of selected lysine residues from the AChE molecule, would therefore require an evaluation of the effect of the lysine removal on enzyme integrity. To this end, the various hypolysine AChE protein products obtained from each of the stable cell lines described before, were quantitified by ELISA, enzymatic activity was determined [Ellman G. L. et al.: Biochem. Pharmacol. 7 (1961) 88-95] and the specific activity of each mutant product was calculated by dividing the enzymatic activity to protein quantity (FIG. 2). In the case of the single and double lysine mutants, the specific activity did not deviate in a significant manner (10-fold deviation) from that of the wild type enzyme (6.5 U/μg). These results indicate that the removal of any of the individual lysine residues does not alter the kinetic performance of the enzyme. Most of the multi-lysine mutants displayed specific activities that are in the range of the single mutants (FIG. 2). Determination of inhibition constants of several OP agents towards selected multilysine AChE mutants, demonstrated that the removal of lysine residues did not alter the reactivity of the mutated AChEs towards OP compounds.

Based solely on this criterion, any of the lysine residues may be eliminated to generate modified AChE for PEGylation, yet pertinent differences in the functional roles of the different lysine residues that were not detected by determining their specific activities, may yet be revealed by subjecting the various hypolysine forms to other examinations. To this end, the various hypolysine mutants were examined for thermal stability, to determine whether some of the lysines play a greater role in maintenance of the physico-chemical integrity of the enzyme, and thereby should not be replaced. This was achieved by incubating the mutated AChEs at 51° C. for various periods of time followed by measurement of residual enzymatic activity. The thermal decay curve of each of the mutant AChE forms was profiled and half-life time values were determined. All of the single and double lysine mutated forms displayed thermal decay values, which did not differ significantly (10-fold deviation) from that of the wild-type enzyme ($T_{1/2}51°$ C.=8.9 min.). Thus, based on two criterions, specific activity and thermostability, we could determine that in the case of AChE, the various lysine residues are not constituents of spatial structures which are critical for enzyme integrity.

Figure 3:
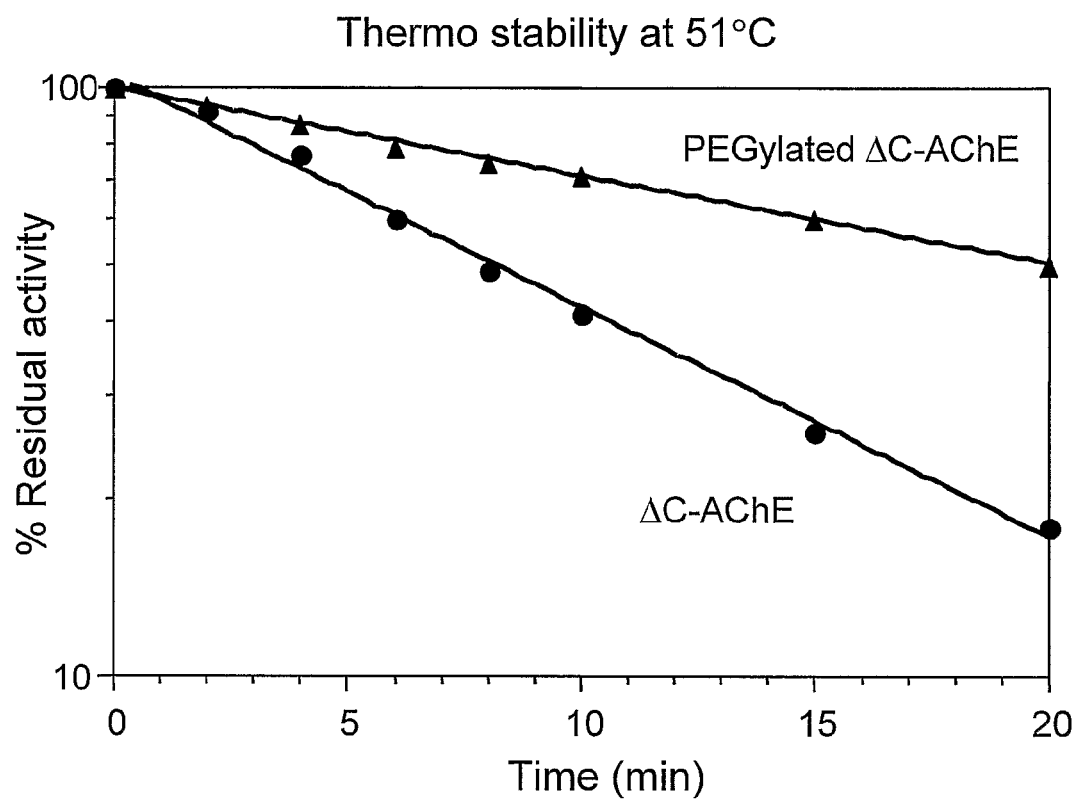
FIG. 3. shows the deactivation at higher temperature of randomly pegylated and unpegylated ΔC-AChE.
Figure 6:
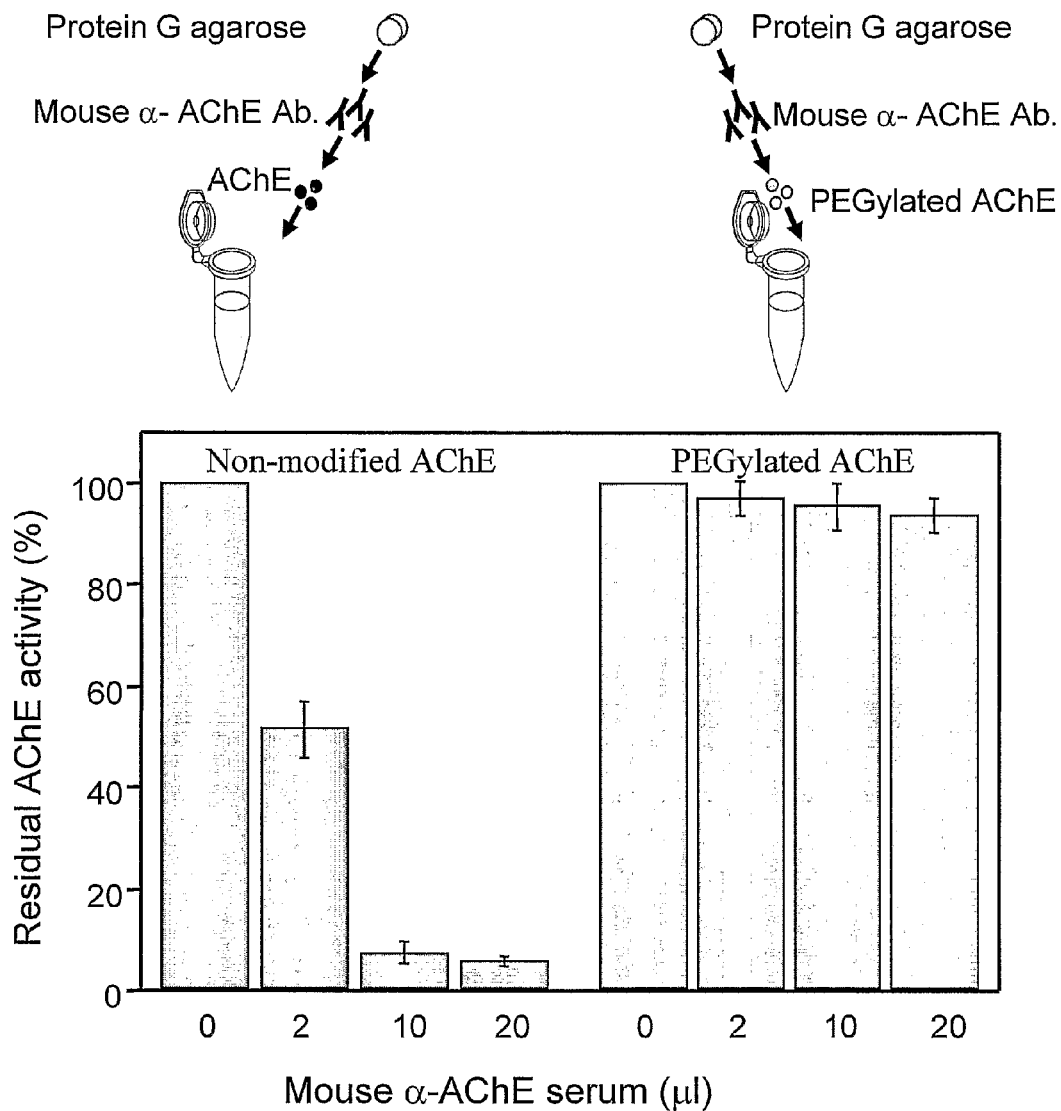
FIG. 6. demonstrates reduced antigenicity of pegylated ΔC-AChE as compared to nonpegylated ΔC-AChE (both species were reacted with polyclonal anti-AChE antibody in vitro, and checked for residual activity after removing immunocomplexes by protein G-agarose)
Figure 7:
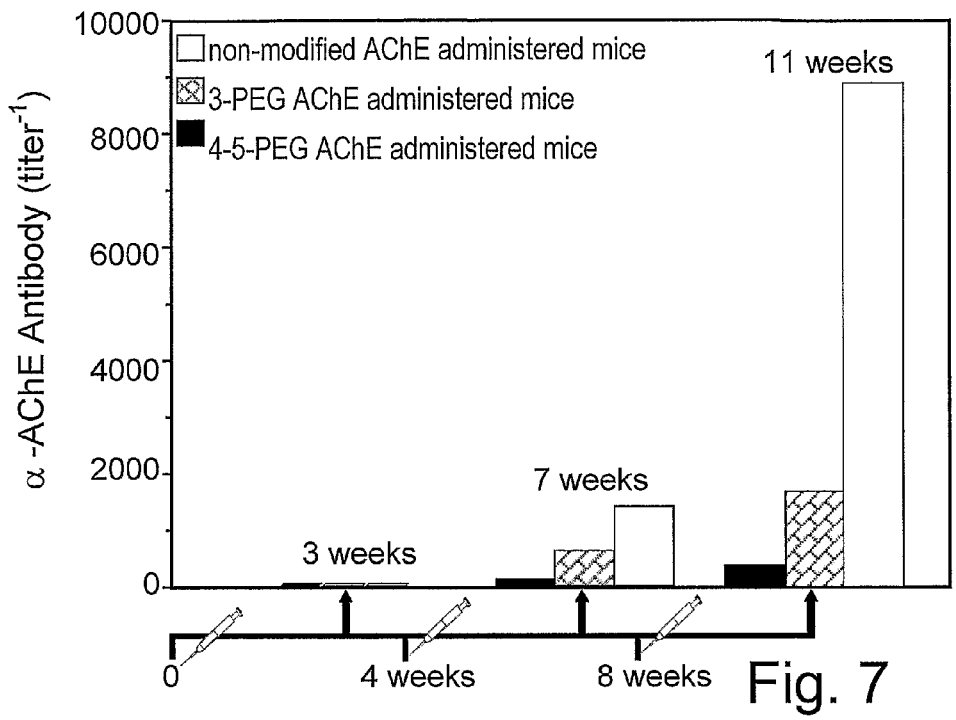
FIG. 7. shows the formation of anti-AChE antibody in mice induced by repeated administering non-pegylated or differently pegylated ΔC-AChE.

Examination of the multi-lysine mutants in which more than 2 lysines were replaced, demonstrated that only enzyme forms which contained the K470A mutation exhibited a slightly more than 10-fold reduction in thermostability as compared to the wild-type enzyme. However, since PEGylated forms of the enzyme are more thermostable than non-modified enzymes (see FIG. 3), the elimination of K470, which affects enzyme stability in a moderate manner only, may prove to have little or no effect at all on the overall performance of hypolysine AChEs in their PEGylated versions. Indeed, as shown in FIG. 6, the pharmacokinetic performance of the PEGylated tetralysine AChE from which K470 was eliminated (K23A/K348A/K470A/K496A) was essentially the same as that of tetralysine AChE in which K470 was not replaced (K23A/K332A/K496A/K538A).

Selective Lysine Residue Elimination

Analysis of the three dimensional model was performed on Silicon Graphics workstation using SYBYL modeling software (Tripos Inc.). The model is based on the three-dimensional structure of ΔC-HuAChE [Kryger et al. 2000].

Determination of the spatial locations of the lysine residues within the 3D model of AChE served as a guideline for choosing selected configurations of mutated hypolysine AChEs, for PEG attachment and subsequent pharmacokinetic analysis. Our working hypothesis was that efficient coverage of the macromolecular surface by PEG chains would require that when the macromolecule is rotated around any of its principal axes, there should always be at least one anchoring point (PEG target site) present at the surface.

Determination of the Preferred Hypolysine PEG-AChE Configuration and its Performance in Mice The hypolysine AChE enzyme forms in which 3 to 7 lysine residues were mutated, were monitored for their pharmacokinetic behavior in mice after PEG-conjugation (FIG. 5). Attachment of PEG chains to primary amines in rHuAChE was performed using succinimidyl propionate activated methoxy PEG (SPA-PEG; Nektar Inc.) as described essentially previously [Cohen O. et al.: Biochem. J. 357 (2000) 795-802; Cohen, O. et al.: Biochem. J. 378 (2004) 117-128]. Clearance experiments in mice (3 to 6 ICR male mice per enzyme sample) and analysis of pharmacokinetic profiles were carried out as described essentially previously [Kronman C. et al.: Biochem. J. 311 (1995) 959-67]. The study was approved by the local ethical committee on animal experiments. Mice were injected with the various rHuAChE preparations (20 μg/mouse in 0.1 ml PBS). Residual AChE activity in blood samples was measured and all values were corrected for background hydrolytic activity in the blood (using samples withdrawn 1 hour before performing the experiment). AChE activity values in samples removed immediately after injection were assigned a value of 100% and used for calculation of residual activity. Background cholinesterase levels in blood of pre-administered mice were less than 2 units/ml. The pharmacokinetic parameters MRT (mean residence time, which reflects the average length of time the administered molecules are retained in the organism) were obtained by analyzing the clearance data according to a noncompartmental pharmacokinetic model using the Win-Nonlin computer program.

Pegylated AChEs containing 1, 2, 3 and 4 target sites for PEG attachment, are characterized in mice by increasing Mean Residue Time values. Enzyme forms which contain the same number of lysine residues, yet differ in the exact lysine positions available for pegylation, are differently cleared from the circulation, as demonstrated by the MRT values of K23A/K53A/K332A/K348A/K496A and 23A/K332A/K348A/K470A/K496A, attesting to the importance of the spatial distribution of the PEG target lysine residues. Optimal pharmacokinetic performance is achieved when the AChE enzyme form includes at least 3 to 4 lysine residues, preferentially 4 lysine residues, available for pegylation.

Determination of the Preferred Hypolysine PEG-AChE Configuration and its Performance in Non-Human Primates The hypolysine AChE enzyme forms in which 3 to 7 lysine residues were mutated, were also monitored for their pharmacokinetic behavior in rhesus monkey (*Macaca mulatta*) after PEG-conjugation (FIG. 5). Treatment of animals was in accordance with regulations outlined in the USDA Animal Welfare Act and the conditions specified in *The Guide for*

Care and Use of Laboratory Animals (National Institute of Health, 1996), and pharmacokinetic studies were approved by the local ethical committee on animal experiments.

Monkeys were injected i.v. with 1000 units of the various AChEs (injection volumes <1 ml/kg). Samples (0.25 ml) of blood were collected at various periods of time in Microtainer tubes (Becton, Dickinson and Co., USA), centrifuged for 1 minute at 10,000 rpm in an Eppendorf microfuge and stored at −20° C. until AChE activity in serum samples was determined. Enzymatic activity was determined following iso-OMPA-mediated BChE inhibition, as described above. AChE activity values in samples removed 2 minutes after injection were referred to as input activities and were used for the calculation of residual activity throughout the experiment. AChE values were corrected for background activity determined in blood samples withdrawn 1 h before performing the experiment. Exogenously administered AChE was at least 20-fold higher than background endogenous iso-OMPA-resistant ChE activity. Analyses of clearance profiles and pharmacokinetic parameters were performed as described for experiments carried out in mice.

Figure 8:
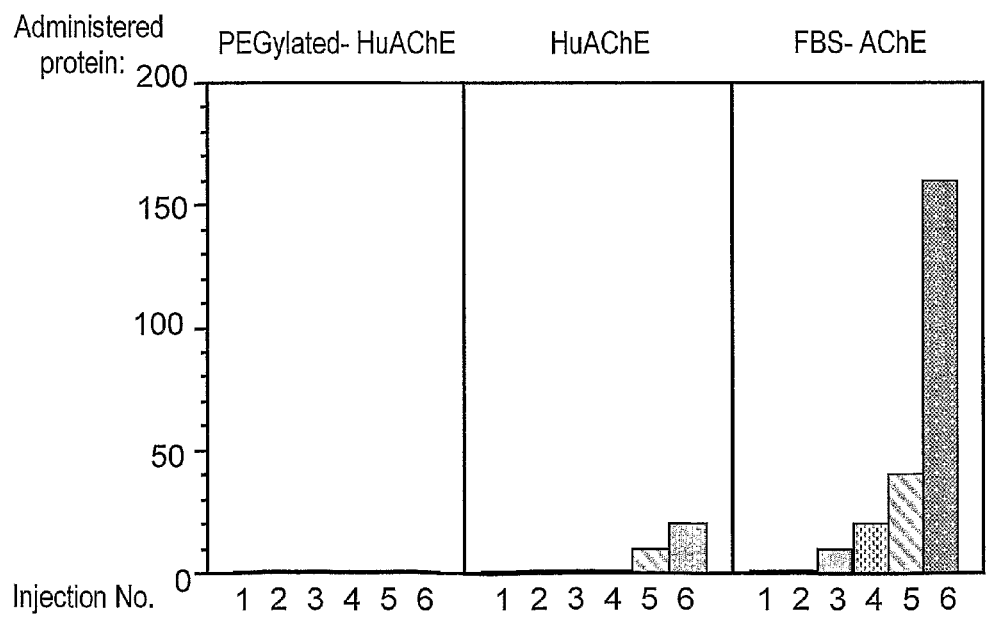
FIG. 8. shows the formation of anti-AChE antibody in monkeys induced by pegylated and two types of native AChEs from different species after repeated injections.

These pharmacokinetic studies demonstrate that the circulatory residence times of the various PEGylated hypolysine AChEs are considerably higher in monkeys (up to 7 days), as compared to mice. Yet, as observed in mice, the Mean Residence Time values of the various hypolysine AChE mutants are affected by the number of lysine residues available for PEGylation. Optimal pharmacokinetic performance, comparable to that of randomly PEGylated ΔC-AChE, is achieved when the AChE enzyme form includes at least 3 to 4 lysine residues, preferentially 4 lysine residues, available for PEGylation. Taken together, these findings indicate that lysine content modulation affects protein pharmacokinetics in a similar manner in various animal models, and therefore the rules for selection of lysines for elimination (based on the criterions of enzymatic activity, protein stability, spatial distribution) are valid throughout, and are not restricted to particular experimental systems.

Evidence for Masking Antigenic AChE Determinants by PEG Attachment

The use of recombinant human AChE or other enzymes as bioscavengers may require repeated administration of these proteins. This may lead to development of antibodies, which in turn, may sequester the bioscavenger from the circulation. The attachment of a linear, flexible uncharged hydrophilic polymer to available but nonessential groups on an enzyme may provide a shell around the enzyme that covers antigenic determinants and, by presenting a flexible hydrophilic surface for inspection by the immune processes, prevents recognition of the interior enzyme as a foreign substance against which an immune response would be induced. Reduced degradation by antigen-presenting cells such as macrophages, shielding of some epitopes of peptides after degradation, or prevention of binding to receptors on B-cells, may all play a role in conferring reduced immunogenicity to the PEG-modified protein [Tsusumi Y. et al.: Proc. Natl. Acad. Sci. USA 97 (2000) 8548-53.

The antigenic properties of pegylated rHuAChE, were studied by incubating 160 ng of either ΔC-rHuAChE or PEGylated rHuAChE with different amounts of polyclonal mouse anti-HuAChE [Shafferman A. et al. J. Biol. Chem. (1992) 17640-48], and then treated with Protein G-Agarose beads. Immunoprecipitation was evaluated by determining residual AChE activity in the supernatant. The results (FIG. 6) clearly demonstrate that, unlike the nonmodified enzyme, the PEGylated version of the enzyme is ineffectively precipitated by the anti-AChE antibodies, demonstrating that the appendage of PEG moieties efficiently "shield" the enzyme from immuno-recognition.

Previous studies have demonstrated that AChE molecules may be eliminated from the circulation by various mechanisms, including receptor mediated asialoglycoprotein removal or species-specific recognition of AChE amino acid epitopes. Circulatory elimination of AChE via these processes was effectively reduced by appendage of PEG moieties to AChE, suggesting that PEGylation provides a protective shield which effectively renders the AChE molecule inaccessible to the various elimination mechanisms. The finding that PEG appendage converts the AChE molecule into a form which is not recognized by anti-AChE antibodies, demonstrates the general nature of the masking provided by PEG, and suggests that this may serve as an effective method for preventing interactions between protein-based therapeuticals and a wide spectrum of host-related mechanisms.

PEG-AChE is Less Immunogenic than Non-Modified AChE in Rodents

To evaluate the effect of PEGylation on the immunological properties of AChE, the immunogenic potential of PEGylated rHuAChE to that of nonmodified rHuAChE was compared, following their administration to mice. To this end, non-modified AChE, 3-PEG AChE and 4-to-5-PEG AChE were repeatedly administered to mice (n=10) at monthly intervals, and anti-AChE antibody formation was monitored (FIG. 7). Mice administered with non-modified AChE displayed substantial levels of anti-AChE antibody even after the second administration (antibody titers=1500 at 7 weeks), and antibody levels increased significantly following the administration of a third dose (antibody titers=9000 at 11 weeks). In contrast, anti-ChE antibody levels were approximately 20-fold lower when 4-to-5-PEG AChE was administered (antibody titers were 130 and 400 at 7 and 11 weeks, respectively). The failure of PEG-AChE to elicit significant antibody formation even in a heterologous animal model (human AChE in mice), demonstrates that the PEG appendage results in the conversion of the AChE molecule into an "immunologically inert" form. Thus, PEG-appendage not only improves the pharmacokinetic properties of AChE, but also effectively shields the enzyme molecules from the host immune system.

Inspection of anti-AChE antibody formation following the administration of 3-PEG AChE (FIG. 7), reveals that antibody levels (antibody titers=660 and 1800 at 7 and 11 weeks, respectively) in this case are still significantly lower than in the case of non-modified AChE (antibody titers=1500 and 9000 at 7 and 11 weeks, respectively), yet they are nevertheless higher than those resulting from the repeated administration of 4-5-PEG AChE (antibody titers=130 and 400 at 7 and 11 weeks, respectively). These results demonstrate that the effective shielding of the AChE molecule from the host immune system depends on the number of target sites available for PEG-appendage, and that low level PEGylation results in the generation of a PEGylated enzyme form with an exposed surface region which may elicit antibody formation. The finding that lysine content modulation determines both the pharmacokinetic and immunogenic properties of the PEGylated enzyme in a similar manner (3-PEG AChE, lower circulatory retention, lower immunological tolerance; 4-5-PEG AChE, higher circulatory retention, higher immunological tolerance) suggests that the rules we have established to select lysine elimination, based on their spatial distribution, should be implemented for the efficient conversion of PEGylated protein pharmaceuticals into homogeneous, immunologically inert molecular forms.

PEG-AChE is Less Immunogenic than Non-Modified AChE in Primates Anti-AChE antibody levels elicited by PEGylated rHuA-ChE, were compared to those induced by nonmodified rHuA-ChE or FBS-AChE, following their administration to rhesus macaques. To this end, non-modified or PEG-modified AChE or the heterologous FBS-AChE (no adjuvant included) were repeatedly administered to monkeys at monthly intervals, and anti-AChE antibody formation was monitored by ELISA (FIG. 8). Repeated administration of the heterologous FBS-AChE led to the development of anti-AChE antibody following the third administration and antibody levels increased significantly following additional administrations. As expected, repeated administration of non-modified, but almost homologous human AChE led to the development of anti-AChE antibody only following the $5^{th}$ administration, but most significantly, repeated administrations of PEGylated human AChE in rhesus macaques failed to elicit a detectable immunogenic response even after the 6th administration. Thus, PEG appendage significantly decreases the immunogenic properties of AChE in non-human primates.

Generation of PEG-Hypolysine AChEs with Improved Bioscavenging Abilities

Figure 9:
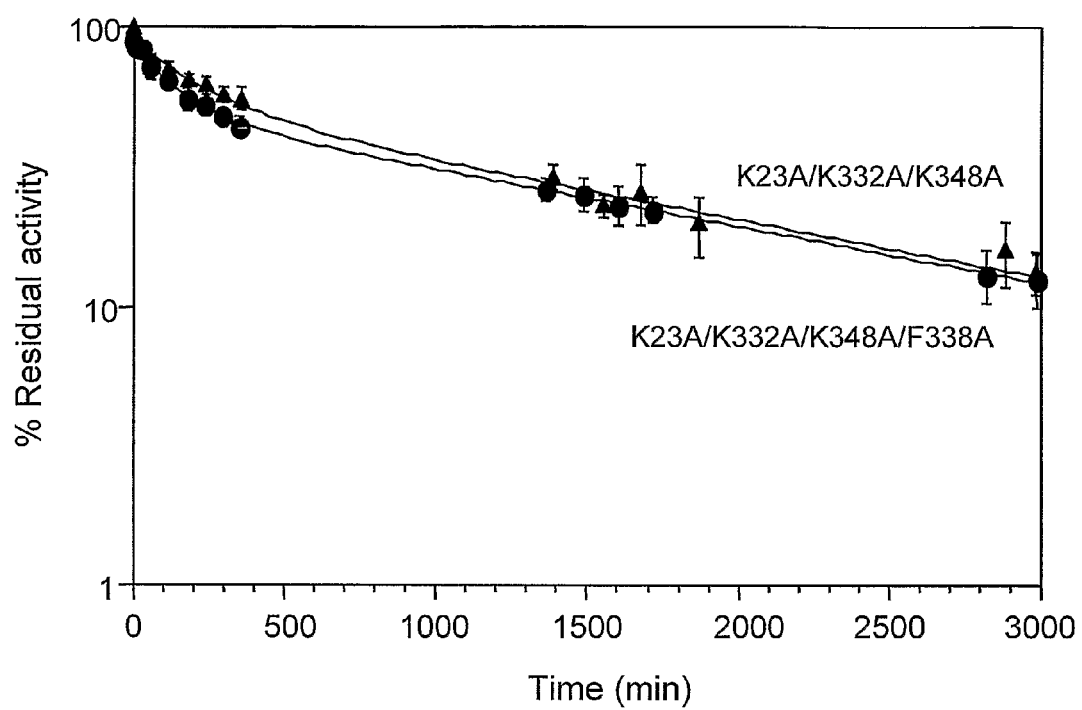
FIG. 9. shows the time dependence of residual activity of a tetralysine ΔC-AChE mutant and of the corresponding F338A mutant, demonstrating that further phenylalanine mutation at position 338 has no deleterious effect on the enzyme stability in the circulation.

Replacement of the phenylalanine residue at position 338 of human AChE by alanine, results in the generation of an enzyme form which displays reduced aging of the somanyl adduct without seriously compromising its reactivity towards soman, and therefore is more effective as an OP bioscavenger [Ordentlich A. et al.: J. Biol. Chem. 271 (1996) 11953-62; Shafferman A. et al.: Biochem. J. 318 (1996) 833-40]. This mutation was incorporated into the tetralysine AChE enzyme to generate the K23A/K332A/K348A/F338A AChE enzyme form. This enzyme species was subjected to PEG conjugation and monitored for its pharmacokinetic performance in mice. As shown in FIG. 9, the modulated enzyme was retained in the circulation in a similar manner to the parent tetralysine AChE, K23A/K332A/K348A. Thus, the diminished "aging" characteristic may be implanted into the hypolysine AChE mold, to generate superior PEG-AChE-based OP bioscavengers. This finding suggests that other kinetic traits may also be introduced into the circulatory long-lived PEG-modified enzyme, to generate optimized enzyme products for therapeutic treatment of OP poisoning.

While this invention has been described in terms of some specific examples, many modifications and variations are possible. It is therefore understood that within the scope of the appended claims, the invention may be realized otherwise than as specifically described.

The invention claimed is:

1. A uniformly pegylated (PEG) human mutant acetylcholinesterase (AChE) lacking all but 2 to 5 lysine residues present in the wild type, being a homogeneous molecular form with organophosphate (OP) scavenging and/or hydrolytic activity, wherein said pegylated mutant (AChE) is obtained by a site directed mutagenesis at the lysine sites, replacing all lysine residues by another amino acid residue, except for 2 to 5 predetermined lysine residues which are pegylated, said predetermined residues is selected in the amino acid sequence of said AChE so that no face on a 3-D model generated for the AChE is devoid of free amino groups for all possible views obtained by rotating the model;

said site-directed mutagenesis includes selecting one part of lysine residues in the AChE amino acid sequence for the PEG-coupling (pegylating) and the other part for said replacing, wherein the selection ensures that the AChE surface shows at least one free amino acid for PEG coupling for all possible views obtained by rotating a 3-D model generated for the hydrolase.

2. The pegylated mutant AChE according to claim 1, where said PEG chains are conjugated to ϵ-amino groups of all remaining lysine residues of said mutant.

3. The pegylated mutant AChE according to claim 1, whose specific activity is at least 10% of the specific activity of the non-mutated non-pegylated enzyme.

4. The pegylated mutant AChE according to claim 1, having reduced immunogenicity.

5. The pegylated mutant AChE according to claim 1, having increased longevity in the mammalian circulation.

6. The pegylated mutant AChE according to claim 1, wherein the PEG has molecular weight of from 200 to 100,000 dalton.

7. The pegylated mutant AChE according to claim 6, wherein the PEG has molecular weight of from 5000 to 20,000 dalton.

8. A method for the preparation of the uniformly pegylated hydrolase of claim 1, comprising
  i) providing a serine hydrolase with organophosphate scavenging or hydrolytic activity with known amino acid sequence;
  ii) selecting the number of PEG chains to be conjugated to the molecule of said hydrolase, and selecting the location of the conjugated chains within said sequence;
  iii) effecting site-directed mutagenesis of said hydrolase, and replacing all lysine residues in the molecule by other amino acid residues, except those lysine residues predetermined in step ii) for conjugating the PEG chains, thereby to obtain a hypolysine mutant of said hydrolase;
  iv) reacting the hypolysine mutant from step iii) with activated PEG; thereby to obtain a uniformly conjugated serine hydrolase with organophosphate scavenging or hydrolytic activity with lowered immunogenicity, and increased stability and longevity in the mammalian circulation.

9. The method according to claim 8, wherein said serine hydrolase with organophosphate scavenging or hydrolytic activity is cholinesterase, comprising
  v) providing a cholinesterase with a known amino acid sequence;
  vi) selecting all possible mutants in which all but n−1 lysine residues are replaced by another amino acid residue, and which have n free amino groups left, including the terminal amino group, for a conjugating reaction, wherein the initial value of n is 3 (dilysine-enzyme);
  vii) generating a three dimensional structure for each of said mutants of step ii), optionally with corresponding two-dimensional representation, comprising marked positions for the terminal amino group and the amino groups of lysine residues;
  viii) examining each mutant of step iii) by rotating its structure sequentially around the X-axis by 90°, Y-axes by 90°, and Z-axes by 90°, providing 12 different rotational positions and 12 corresponding two-dimensional front views, evaluating each position as positive if there is at least one free amino group inside the front view, and as negative if there is no free amino group inside the front view;
  ix) discarding all the mutants evaluated as negative in at least one of said 12 rotational positions, and selecting one of the mutants evaluated as positive in all 12 positions for real mutant construction; or, if all the potential mutants were discarded, continuing by step ii) in which the value of n is increased by 1 (trilysine-cholinesterase and higher) through steps iii) to v);

x) constructing said selected mutant from step v) by using known methods for mutating and expressing recombinant proteins, thereby obtaining a recombinant hypolysine enzyme mutant; and xi) reacting said mutant from step vi) with a non-immunogenic polymer, such as PEG, under conditions enabling to couple a chain of said polymer to each of said free amino groups;

thereby to obtain uniformly conjugated protein with lowered immunogenicity, and increased stability in mammalian circulation.

10. The method according to claim 9, further comprising viii) repeating steps ii) to vii) using more values of n in order to obtain additional uniformly conjugated mutant proteins; and ix) evaluating the conjugated mutant proteins to determine a desired property; and x) selecting the best one for a large scale production.

11. The method according to claim 8, further comprising effecting another mutation, unrelated to the lysine replacements, which improves desired properties of the mutant, the properties selected from the group consisting of specific activity, thermal stability, antigenicity, immunogenicity, stability in mammalian circulation, and longevity in mammalian circulation.

12. The method according to claim 8, wherein the PEG comprises an activated methoxypolyethylene glycol having molecular weight of from about 200 to about 100,000 dalton.

13. The method for the preparation of a uniformly pegylated hydrolase according to claim 9, wherein said hydrolase is acetylcholinesterase (AChE), and said selected number of PEG chains to be conjugated is from 3 to 5.

14. The method according to claim 13, wherein the pegylated AChE has a half-life in mouse circulation of 2 hours or more.

15. The pegylated mutant AChE according to claim 1 for use as a detoxifying agent.

16. A pharmaceutical composition for treating or preventing OP poisoning, comprising the pegylated mutant AChE according to claim 1, and further comprising pharmaceutically acceptable carrier, diluent, adjuvant, or excipient.

17. The pegylated mutant AChE according to claim 5, having a half-life in mouse circulation of 2 hours or more.

18. The pegylated mutant AChE according to claim 1, wherein said replacing the predetermined two to five lysine residues comprises i) generating a three dimensional structure for each possible mutant in which all but two to five lysine residues are replaced by another amino acid residue, ii) examining each mutant by rotating its structure sequentially around the X-axis by 90°, Y-axes by 90°, and Z-axes by 90°, providing 12 different rotational positions and 12 corresponding two-dimensional front views, and iii) evaluating each position as positive if there is at least one free amino group inside the front view, wherein there are totally three to six free amino groups when including the terminal amino group.

19. The pegylated-mutant AChE according to claim 18, wherein said replacing the predetermined two to five lysine residues further comprises selecting one of the mutants evaluated as positive in all 12 positions for real mutant construction and pegylating it at each of said free amino groups, thereby obtaining uniformly conjugated protein with lowered immunogenicity, and increased stability in mammalian circulation.

20. The pegylated mutant AChE according to claim 19, wherein said replacing the predetermined two to five lysine residues further comprises selecting more mutants evaluated as positive in all 12 positions for real mutant construction and pegylating them, thereby obtaining uniformly conjugated proteins of which the best is selected for a large scale production.

21. The pegylated mutant AChE according to claim 20, further comprising another mutation, unrelated to the lysine replacements, improving desired properties of the mutant, the properties selected from the group consisting of reactivity toward OP compounds, specific activity, reactivation of OP-enzyme conjugates, thermal stability, antigenicity, immunogenicity, stability in mammalian circulation, and longevity in mammalian circulation.

22. The pegylated mutant AChE according to claim 18, wherein said mutant comprises from 3 to 6 PEG chains coupled at predetermined sites via remaining amino groups to said AChE mutant in which from 2 to 5 lysine residues are replaced by other amino acid.

23. The pegylated mutant AChE according to claim 22, wherein said AChE is human recombinant enzyme.

* * * * *